United States Patent [19]

Summers et al.

[11] Patent Number: 5,622,654

[45] Date of Patent: Apr. 22, 1997

[54] NLO DYE COMPOSITIONS AND USE THEREOF IN PRODUCING NLO ELEMENTS

[75] Inventors: John D. Summers, Newtown Square; Wilson Tam, Boothwyn, both of Pa.

[73] Assignee: E. I. Du Pont de Nemours and Company, Wilmington, Del.

[21] Appl. No.: 602,394

[22] Filed: Feb. 16, 1996

Related U.S. Application Data

[62] Division of Ser. No. 860,863, Mar. 31, 1992, Pat. No. 5,534,201.

[51] Int. Cl.⁶ .............................. F21V 9/00; C07D 401/00
[52] U.S. Cl. .............................................. 252/582; 544/300
[58] Field of Search ............................... 252/582; 544/300

[56] References Cited

U.S. PATENT DOCUMENTS

| | | | |
|---|---|---|---|
| 5,156,774 | 10/1992 | Leising et al. | 252/582 |
| 5,272,218 | 12/1993 | Cheng et al. | 252/582 |

FOREIGN PATENT DOCUMENTS

| | | | |
|---|---|---|---|
| 214828 | 3/1987 | European Pat. Off. | G02F 1/35 |
| 0384811 | 8/1990 | European Pat. Off. | C07D 333/24 |
| WO91/13116 | 9/1991 | WIPO | C08K 5/00 |

OTHER PUBLICATIONS

Wu, J. W. et al, *J. Appl. Phys.*, 69(10), 7366–7368 (1991).
Valley, J.F. et al, *Appl. Phys Lett.*, 60(2), 160–162 (1992).
Singer, K.D. et al, *Appl. Phys. Lett.*, 49(5), 248–250 (1966).
Stähelin, M. et al, *Appl. Phys. Lett.*, 61(14), 1626–1628 (1992).
Stenzenberger, H. in D. Wilson et al, (Ed.), *Polyamides*, Blackie & Son, Ltd., London, 79–128 (1990).
Ermer, S. et al, *Polym. Preprint*, 32(3), 92–93 (1991).
Wu, J.W. et al, *Appl. Phys. Lett.*, 58(3), 225–227 (1991).
Hampsch, H. L. et al, *Polymer Comm.*, 30, 40–43 (1989).

*Primary Examiner*—Philip Tucker

[57] ABSTRACT

Nonlinear optical elements are disclosed which comprise a polyimide which is solution and/or melt processable, and a poled NLO dye. Also disclosed is a process for making such elements, and devices in which they can be used. Disclosed NLO dyes include

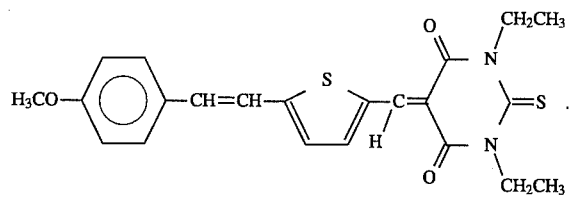

1 Claim, No Drawings

NLO DYE COMPOSITIONS AND USE THEREOF IN PRODUCING NLO ELEMENTS

This is a division of application Ser. No. 07/860,863, filed Mar. 31, 1992 now U.S. Pat. No. 5,534,201.

FIELD OF THE INVENTION

This invention relates to nonlinear optical (NLO) dyes and their use in combination with polymer hosts in nonlinear optical elements.

BACKGROUND OF THE INVENTION

Nonlinear optical dyes (organic molecules having large nonlinear polarizabilities) have been recognized as potentially useful as components of the optical elements in optical frequency converters and in electrooptic devices. Generally, in order for the NLO dyes to exhibit the large second order optical susceptibilities essential to nonlinear optic applications, the molecules must be constructively arrayed in a noncentrosymmetric configuration. Such molecules have been crystallized in a noncentrosymmetric space group, but this method does not work for all potentially useful molecules, and the resulting shape and properties are limited by the very nature of a crystal.

The NLO dyes have been used, for example, in combination with glassy polymers to provide nonlinear optical elements. The choice of the dye molecule and glassy polymer affects the stability of nonlinear optical effect obtained, because the dye molecules have a tendency to "relax" over time, thereby losing the configuration necessary for the enhanced nonlinear optical properties.

The use of certain amorphous thermoplastics as hosts for NLO dyes in nonlinear optical elements is known, see for example H. L. Hampsch, et al., Polym. Commun., vol. 30, p. 40–43 (1989).

The electrical properties and chemical stability of a glassy polymer used in optical elements are important, since these characteristics are relevant to the efficient functioning of devices in which the nonlinear optical elements are generally employed. Thus, when choosing a host polymer for NLO dyes, pertinent properties for consideration include low water absorption, thermal and chemical stability, dielectric constant, and thermal coefficient of expansion. Polyimides are often used in electronics applications since many of their properties makes them especially suited for such uses.

S. Ermer, et al., Polym. Prepr., vol. 32, p. 92–93 (1991) and J. W. Wu, et al., Appl. Phys. Lett., vol. 58, p. 225–227 (1991) dissolved NLO dyes in polyamic acid precursors to polyimides, and while heating the mixture to high temperatures to form the final polyimide polymer, poled it in an electric field to align the dye molecules. The polyimides produced in these publications are not processible (i.e., they are insoluble and/or decompose before melting). Moreover, the high temperatures employed in converting the polyamic acid to the polyimide, are considered conducive to significant undesirable sublimation and/or chemical decomposition of the dye molecules.

SUMMARY OF THE INVENTION

A nonlinear optical element is provided in accordance with this invention which comprises a blend of a processible polyimide and an NLO dye wherein said NLO dye is aligned in conformance with an externally applied electric field. This invention also provides a process for the production of a nonlinear optical element, comprising (a) mixing a processible polyimide with an NLO dye so that a blend is formed; and (b) poling the blend to align the NLO dye in conformance with an externally applied electric field.

This invention also provides a compound of the formula

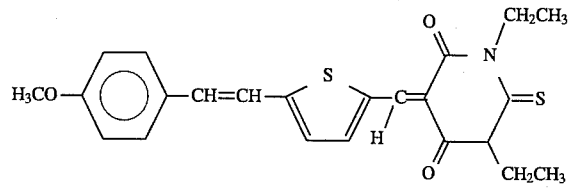

which is useful as an NLO dye.

DETAILS OF THE INVENTION

This invention provides compositions comprising two essential materials: a processible polyimide; and an NLO dye. Polyimides are a well known class of polymers. A "processible polyimide" as used herein means a polyimide that (without substantial decomposition of the polyimide) is soluble in common organic solvents and/or is melt processible.

For processible polyimides which are soluble, solutions may be formed simply by dissolving the polymer in the organic solvent. This may be done at any convenient temperature, but solutions are preferred where the solution temperature is about 100° C. or less, and more preferred if the solution temperature is around ambient temperature (i.e., about 25° C.). Typical organic solvents include N-methylpyrrolidone; N,N-dimethylformamide; and dimethylsulfoxide. N-methylpyrrolidone is considered particularly suitable.

Processible polyimides which are melt processible (i.e., they can be processed in the melt or liquid phase by typical melt forming techniques, such as extrusion, injection molding, and casting) have glass transition temperatures (Tg) below their thermal decomposition points. Normally melt processing is conducted at or above the Tg of the polyimide. It is preferred if the temperature employed for melt processing of the polyimide is about 250° C. or less, more preferably about 200° C. or less. Even if the temperature used for melt processing the polyimide is relatively high, the short processing times typically required for melt processing (often about 1 to 3 min.), will often result in little significant decomposition of an NLO dye mixed into the molten polyimide.

The processible polyimide used should have a Tg above ambient temperature, preferably about 100° C. or more, more preferably 150° C. or more. The processible polyimide should not contain any significant amount of crystallinity; that is the polyimide should be essentially amorphous, and any crystallites present therein should be small enough not to scatter the incoming light that is absorbed during NLO operation. The polyimides useful in the present invention are known to the skilled artisan, and can be made by known methods. Examples of such polyimides are those having repeat units selected from the group consisting of

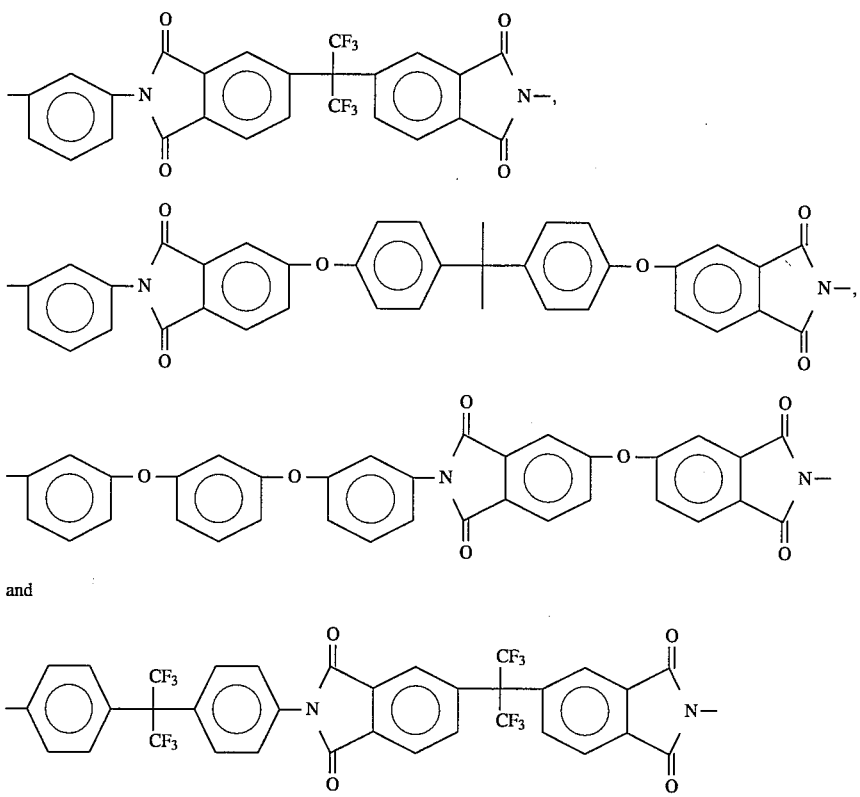

The processible polyimides useful in this invention include certain addition polyimides which can be crosslinked by heating them to a sufficiently high temperature (typically about 250° C. or less) or by other means (e.g., microwave radiation). Addition polymers are known, and typically contain chemical groups that upon curing, serve to crosslink the polymer molecules. (See e.g., H. Stenzenberger in D. Wilson et al., Ed., Polyimides, Blackie & Son Ltd., London, 1990, pp. 79–128). Generally, the fully crosslinked polyimide is no longer processible (i.e., it is relatively insoluble and is not melt processible). Accordingly, care should be exercised not to substantially crosslink the addition polyimides prior to forming blends thereof with NLO dyes in accordance with this invention.

Nonlinear optical dyes (i.e., NLO dyes) are a known class of compounds characterized by their molecular hyperpolerizability. Generally the NLO dyes employed in this invention have a molecular hyperpolarizability ("beta") of greater than about $10^{-30}$ electrostatic units (esu) measured by conventional EFISH methods, as described in L. T. Cheng, et al., SPIE, vol. 1147, p. 61–72 (1989) which is incorporated herein by reference. NLO dyes often have three subunits, arranged A-E-D where A is an electron acceptor group (e.g., cyano, nitro, or perfluoroalkyl-sulfonyl), D is an electron donor group (e.g., amino or alkoxy), and E is a group having a conjugated pi bond system. These groups are arranged within the dye so that it has noncentrosymmetric molecular dipoles having an electron donor group linked through a pi-bonding system to an electron acceptor group. Such NLO dyes and their structural requirements, are well known to those skilled in the art, see for example L. T. Cheng et al., supra, and J. F. Nicoud et al., in D. S. Chemla and J. Zyss, Ed, Nonlinear Optical Properties of Organic Molecules and Crystals, Vol. 1, Academic Press, New York, 1987, p. 227–296.

Any NLO dye chosen should be soluble in the organic solvent used in making the blend and/or be thermally stable at the temperature required to melt mix the polyimide and dye (see below). Examples of useful NLO dyes are

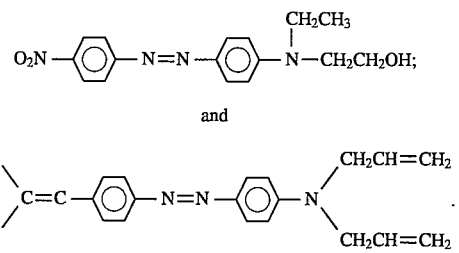

A unique compound provided in accordance with this invention which can be used as an NLO dye is represented by the structural formula

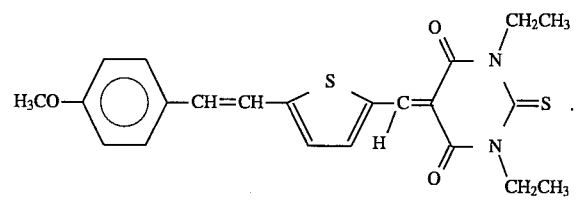

This compound is made by palladium cross-coupling of 5-bromo-thiophenecaboxaldehyde with vinylanisole, followed by base-catalyzed condensation of the resulting aldehyde with 1,3-diethyl-2-thiobarbituric acid in ethanol.

For the nonlinear optical elements provided by this invention, the polyimide and NLO dye are mixed to make a "blend". By blend herein is meant the NLO dye is incorporated into the processible polyimide. Blend does not mean a simple physical mixture of particles of the NLO dye and separate particles of the polyimide. In many cases the NLO dye will be dissolved or molecularly dispersed in the polyimide, and that is preferred. It is also preferred to uniformly disperse the NLO dye in the polyimide.

This invention also includes a process for making a nonlinear optical element. One step of this process involves mixing an NLO dye with a processible polyimide to form a blend. This can be done either in solution or by melt processing. To form the blend via a solution the polyimide is dissolved in a solvent along with the NLO dye. This may be done in any order and either separately, in which case the solutions are mixed, or together. After a solution in which both the polyimide and NLO dye are dissolved is formed, the solvent is removed by any convenient method, such as evaporation or vacuum drying. A typical form for an NLO element is a film, so a film may be formed the same time the solvent is evaporated, as by spin coating or forming a film with a doctor knife.

The concentration of the polymer and NLO dye in solution is not critical. It is usually desirable to obtain as high a concentration of NLO dye in the processible polyimide as possible, so this should be kept in mind when dissolving the components. In order to avoid the necessity of removing large volumes of solvents, it is desirable to use relatively high concentrations of polyimide and NLO dye, but other factors such as the solubility limits of the NLO dye and solution viscosity due to the polyimide can place a practical upper limit on the concentrations that are conveniently used. Temperature is not critical, although elevated temperatures may be needed to dissolve one or both components.

Another method of making the blend is melt mixing. In this method the polymer is heated into a melt, and agitation is applied to mix in the NLO dye. The NLO dye should preferably be soluble in the polymer at the mixing temperature. The NLO dye should also be reasonably stable under the mixing conditions (time and temperature). Although the polyimide may simply be heated and mixed in a simple vessel, it is well known to use screw melters to melt polymers, such as screw extruders or injection molding machines. These offer the advantage of thorough melting and mixing in relatively short time periods. They can also be used to form the final element shape, such as extruding a film. The melt mixing should be done above the Tg of the polyimide.

Another step of the process involves aligning the NLO dye molecules in conformance with an externally applied electric field. This alignment may be carried out simultaneous with the formation of the polyimide-NLO dye blend or after the blend is formed. It will usually also be done simultaneous with or after the blend has been made into the final element shape such as a film. Substantially locking the NLO dye molecules in a biased alignment is referred to as poling. Poling can be carried out by subjecting the blend to an electric field. It is preferred to align when the dye molecules are relatively mobile, as when solvent has not been completely removed and/or at elevated temperatures (e.g., above about 120° C.; but below the temperature at which significant NLO dye degradation or sublimation takes place). Preferably poling is accomplished above the Tg of the polyimide. The alignment can be "locked in" by continuing to apply the electric field until the mobility of the NLO dye molecules is reduced, as by removal of all solvent and/or cooling the blend.

An electric field for poling is commonly provided by either corona poling or electrode poling. In electrode poling the electric field is created between two closely spaced electrodes. Depending on the desired sample configuration, these electrodes can either be in the plane of a thin film, in which case the field is primarily parallel to the surface of the sample; or it can be in a plane above and below the sample, in which case the field is perpendicular to the sample surface. The latter configuration has the advantage of generating high fields over a large area, but has the disadvantage for frequency doubling of requiring that the electrodes are transparent (transparency required only to measure transmitted SHG light) and that the sample is tilted with respect to the input beam. This latter requirement is necessary so that a component of the fundamental beam's electric field can be parallel to the poling direction.

Electrode poling has several disadvantages, particularly when surveying a large number of new materials where the thin film quality and characteristics have not been optimized. Because of the high fields involved, electrochemistry can take place at the electrodes, thereby altering material properties. Also microscopic defects can lead to electrical breakdown at potentials many times smaller than a defect-free film could sustain. Such a breakdown will typically ruin a sample since the entire charge contained on the electrodes will flow through a small area of the sample causing thermal damage not only to the sample but also to the electrodes.

Corona poling avoids these disadvantages. A corona discharge is used to create the electric field by depositing charge on a thin film sample which has been coated on a conductive substrate. Corona poling eliminates the high voltage electrode. Since there is no conductive electrode to carry charge to a defect, the catastrophic damage associated with having a conductive point defect is also eliminated. This technique does, however, have the limitations of requiring a transparent (transparency required only to measure transmitted SHG light) electrode and a tilted sample. In addition, since a corona discharge is a current limited source, modest sample conductivity will cause a reduction in the maximum field which can be generated. For a discussion of corona poling, see, e.g., K. D. Singer et al., "Electro-optic phase modulation and optical second harmonic generation in corona-poled polymer films", Appl. Phys. Lett. 53(19) pp. 1800–1802 (1988).

The poled blends of this invention are considered particularly useful because of their high concentration of nonlinear optically active molecules, their capability of being formed into large area thin films, and their high orientational stability. Preferred film thickness can vary according to use. Typically film thickness is within the range of 0.5 μm–2 μm.

When addition polyimides are used, the poled blends may be crosslinked after they are formed into the desired shape. Accordingly, to form an optical element, a processible addition polyimide may be dissolved in solution and/or melt processed to form a blend with an NLO dye; the blend may be formed into the desired shape (e.g., formed into a film) and poled; and the polyimide of the poled and shaped blend may be crosslinked. Crosslinking using heat curing may be accomplished during poling.

The poled blends can also be provided in forms other than films (e.g., a solid block of polymer could be formed into an electrooptic modulator or a frequency converter using conventional techniques known in the art for single crystals) and poled blends in various forms are included within this invention.

The poled blends of this invention are preferably shaped to function as nonlinear optical elements for transforming electromagnetic radiation (e.g., by changing the frequency and/or polarization of the radiation). Generally, the nonlinear optical element of a poled blend is used for transforming electromagnetic radiation by including it within an optical device. A device for transforming electromagnetic radiation using a nonlinear optical element is described in U.S. Pat. No. 4,909,964. The present invention may be used in such a device.

A conventional nonlinear optical device disclosed in U.S. Pat. No. 4,909,964 comprises means to direct at least one incident beam of electromagnetic radiation into an element. The element has nonlinear optical properties whereby electromagnetic radiation emerging from the element contains at least one frequency different from the frequency of any incident beam of radiation. The different frequency is an even multiple of the frequency of one incident beam of electromagnetic radiation.

Preferably, the emerging radiation of a different frequency is doubled (second-order) (SHG). Preferably, the electromagnetic radiation is radiation from one of a number of common lasers, such as Nd-YAG, Raman-shifted Nd-YAG, Nd-YLF or Nd-glass, semiconductor diode, Er-Glass, Ti-Sapphire, dye, and Ar or Kr ion, or radiation shifted to other frequencies by nonlinear processes. For example, polarized light of wavelength 1.06 μm from an Nd-YAG laser is incident on the optical element along the optical path. A lens focuses the light into the optical element. Light emerging from the optical element is collimated by a similar lens and passed through a filter adapted to remove light of wavelength 1.06 μm while passing light of wavelength 0.53 μm.

As disclosed in U.S. Pat. No. 4,909,964 (incorporated herein by reference), one conventional electro-optic modulator comprises means to direct a coherent beam into an optical element, and means to apply an electric field to the element in a direction to modify the transmission property of the beam. For example, in an electro-optic modulator comprising an optical element, a pair of electrodes is attached to the upper and lower surfaces of the element, across which a modulating electric field is applied from a conventional voltage source. The optical element is placed between two polarizers. A light beam (such as that from a Nd-YAG laser) is polarized by a polarizer, focused on the optical element and propagated therethrough, and subjected to modulation by the electric field. The modulate light beam is led out through an analyzer polarizer. Linearly polarized light traversing the optical element is rendered elliptically polarized by action of the applied modulating voltage. The analyzer polarizer renders the polarization linear again. Application of the modulating voltage alters the birefringence of the optical element and consequently the ellipticity impressed on the beam. The analyzer polarizer then passes a greater or lesser fraction of the light beam as more or less of the elliptically polarized light projects onto its nonblocking polarization direction.

It will be further apparent to those skilled in the art that the optical elements formed by the poled blends of the present invention are useful in this and other devices utilizing their nonlinear properties, such as devices utilizing the electro-optic effect.

Practice of the invention will become further apparent from the following non-limiting examples.

EXAMPLES

In these Examples, EtOH means ethanol; NMP means N-methylpyrrolidone; and SHG means second harmonic generation.

In the Examples, the following polyimides are used. The references given with the polyimides are references to them in the literature. Inherent viscosities are measured at 30° C. as a 0.5 weight percent solution in N-methylpyrrolidine.

Polyimide A

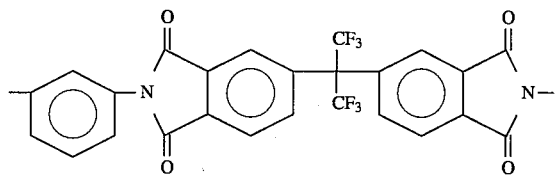

Tg=300° C.
ηinh=1.51
St. Clair et al., in Harris and Seymour, Ed. Structure-Solubility Relationships in Polymers, Academic Press, New York, 1977, p. 199.

Polyimide B

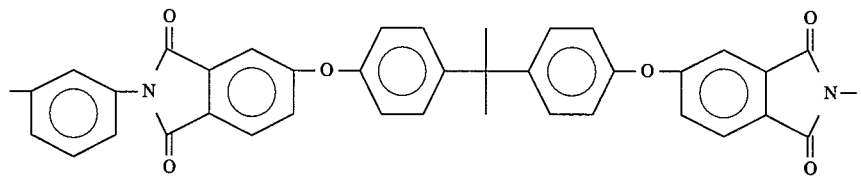

Tg–217° C.
η=0.43
This is Ultem® 1000, Trademark of and available from General Electric Co.

Polyimide C

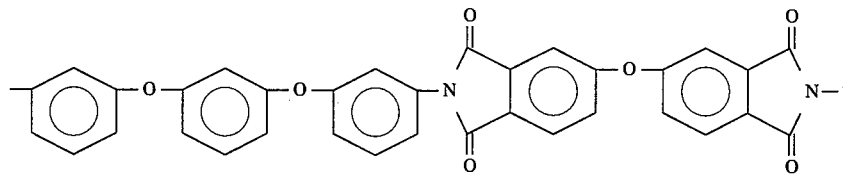

Tg=183° C.
η=0.75
European Patent Application 299,865

Polyimide D

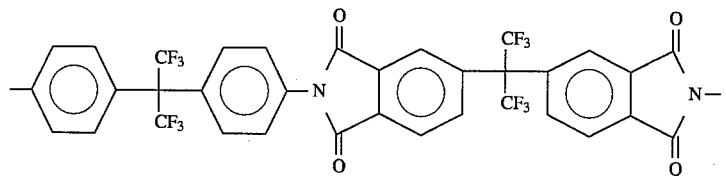

Tg=314° C.
η=0.98
Obtained from American Hoechst.

In the Examples in which an NLO element is formed from solution, the amount of solvent used was typically 15–30 drops.

In the Examples, Disperse Red 1 means the following NLO dye:

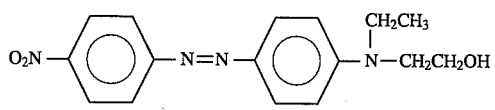

In the Examples, the poling apparatus consists of a sample holder constructed so that the sample normal is 45° to the beam direction. The laser beam is polarized so that the electric vector is in the plane defined by the sample normal and the beam. Heaters are incorporated into the sample holder so that the temperature of the sample can be maintained anywhere in the temperature range from room temperature to 200° C. A standard corona charging unit from a xerographic copy machine is positioned over the sample to apply an electric field. Appropriate holes are cut in the sample holder and the corona charging unit to allow both the fundamental beam and any second harmonic light to pass through the sample and be detected.

Example 1

Disperse Red 1 (15 mg) and 50 mg of Polyimide A were dissolved in NMP and films were cast. The films were heated on a hot plate at 150° C. and then vacuum dried at 140° C. overnight. The film was poled at 171° C. and then cooled to 46° C. The field was removed and the sample placed in an 80° C. oven. The SHG signal at 80° C. was 28% of the maximum SHG signal observed during the poling process. This SHG signal was observed to be stable at 80° C. for 10 days. The sample was placed in a 100° C. oven. The SHG signal was 11% of the maximum SHG signal observed during the poling process. This SHG signal decreased by about 0.9%/day at 100° C.

Another film was poled to 167° C. and then cooled to 70° C. The field was removed and the sample placed in an 80° C. oven. The SHG signal at 80° C. was 39% of the maximum SHG signal observed during the poling process. This SHG signal was observed to be stable at 80° C. for 10 days. The sample was placed in a 100° C. oven. The SHG signal decreased by about 0.9%/day at 100° C.

Example 2

Disperse Red 1 (15 mg) and 50 mg of Polyimide B were dissolved in NMP and films were cast. The films were heated on a hot plate at 160° C. and then vacuum dried at 140° C. for two hours. A film was poled at 160° C. and then cooled to 70° C. The field was removed and the sample placed in an 80° C. oven. The SHG signal at 80° C. was 47% of the maximum SHG signal observed during the poling process.

This SHG signal was observed to be stable at 80° C. for 20 days. The sample was placed in a 100° C. oven. The SHG signal decreased by about 0.8%/day at 100° C.

Example 3

Disperse Red 1 (15 rag) and 50 mg of Polyimide C were dissolved in NMP and films were cast. The films were heated on a hot plate at 160° C. for two hours. A film was poled at 160° C. and then cooled to 35° C. The field was removed and the sample placed in an 80° C. oven. The SHG signal at 80° C. was 45% of the maximum SHG signal observed during the poling process. This SHG signal was observed to be stable at 80° C. for 20 days. The sample was placed in a 100° C. oven. The SHG signal was decreased by about 0.9%/day.

Example 4

Disperse Red 1 (15 mg) and 50 mg of Polyimide D were dissolved in NMP and films were cast. The films were heated on a hot plate at 160° C. and vacuum dried overnight at 130° C. A film was poled at 180° C. and then cooled to 80° C. The field was removed and the sample placed in an 80° C. oven. The SHG signal at 80° C. was 31% of the maximum SHG signal observed during the poling process. This SHG signal was observed to be stable at 80° C. for 16 days. The sample was placed in a 100° C. oven. The SHG signal decreased by about 0.8%/day.

Example 5

(Dicyanovinyl)benzenediazonium hexafluorophosphate, 0.795 g (2.44 mmoles), (prepared according to literature: M. L. Schilling, H. E. Katz, and D. I. Cox, J. Org. Chem. 1988, 53, 5538) was added to 15 ml of water and 15 ml of glacial acetic acid. The mixture was cooled in an ice bath and 0.423 g (2.44 mmoles) of N,N-diallylaniline was added. After stirring for 15 minutes, 0.50 g of sodium acetate was added and the mixture warmed to room temperature and stirred overnight. The product was collected and washed with 5 ml of water to give 0.402 g of the desired product. $^1$H nmr(CD$_2$Cl$_2$): 7.9 (m, 7H), 6.8 (m, 2H), 5.9 (m, 2H), 5.2 (m, 4H), 4.1 (m, 4H).

Example 6

Fifteen mg of the product of Example 5 and 50 mg of Polyimide D were dissolved in NMP and films were casted. The films were heated on a hot plate at 150° C. and vacuum dried overnight at 130° C. A film was poled at 200° C. and then cooled to room temperature. The field was removed and the sample placed in an 80° C. oven. The SHG signal at 80° C. was 49% of the maximum SHG signal observed during the poling process. This SHG signal was observed to be stable at 80° C. for 6 days. The sample was placed in a 100° C. oven. The SHG decreases by about 0.7%/day at 100° C.

Example 7

Fifteen mg of the product of Example 5 and 50 mg of Polyimide B were dissolved in NMP and films were cast. The films were heated on a hot plate at 150° C. and vacuum dried overnight at 130° C. A film was poled at 195° C. and then cooled to 66° C. The field was removed and the sample placed in an 80° C. oven. The SHG signal at 80° was 58% of the maximum SHG signal observed during the poling process. This SHG signal was observed to be stable at 80° C. for 15 days. The sample was placed in a 100° C. oven. The SHG signal was 40% of the maximum SHG signal observed during the poling process. This SHG signal decreased by about 0.7%/day.

Example 8

Fifteen mg of the product of Example 5 and 50 mg of Polyimide C were dissolved in NMP and films were cast. The films were heated on a hot plate at 155° C. and vacuum dried overnight at 130° C. A film was poled at 159° C. and then cooled to 50° C. The field was removed and the sample placed in an 80° C. oven. The SHG signal at 80° C. was 56% of the maximum SHG signal observed during the poling process. This SHG signal was observed to be stable at 80° C. for 10 days. The sample was placed in a 100° C. oven. The SHG signal was decreased by about 1% day.

Example 9

Reaction of 5-bromo-2-thiophenecarboxaldehyde with 4-vinylanisole:

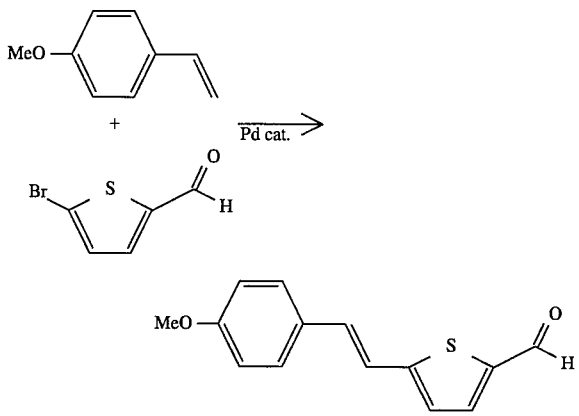

The cross-coupling of 5-bromo-2-thiophenecarboxaldehyde with vinylanisole was performed according to a similar procedure described in W. C. Frank, Y. C. Kim, and R. F. Heck, J. Org. Chem., 43,2947 (1978). One gram (5.23 mmoles) of 5-bromo-2-thiophenecarboxaldehyde, 0.900 g (6.71 mmoles) of 4-vinylanisole, 31 mg (0.14 mmoles) of palladium acetate and 72 mg (0.236 mmoles) of tri-o-tolylphosphine were placed in 6 ml of $NEt_3$. The mixture was placed in a 100° C. bath overnight; the reaction was kept under nitrogen. To the mixture was added 25 ml of water and the mixture was extracted 3×75 ml of $CH_2Cl_2$. The organic extract was washed with 2×10 ml of water and then dried over $MgSO_4$. The solution was filtered, solvent removed by rotary evaporation and the residue chromatographed on silica gel eluted with $CH_2Cl_2$. A yellow band was collected to give 0.397 g (1.62 mmoles, 31%) of the desired coupled product. $^1H$ nmr ($CD_2Cl_2$): 9.82 (s, 1H), 7.66 (d, J=3.9 Hz, 1H), 7.47 (m, 2H), 7.14 (d,J=3.9 Hz, 1H), 7.13 (s, 2H), 6.91 (m, 2H), 3.82 (s, 3H).

Example 10

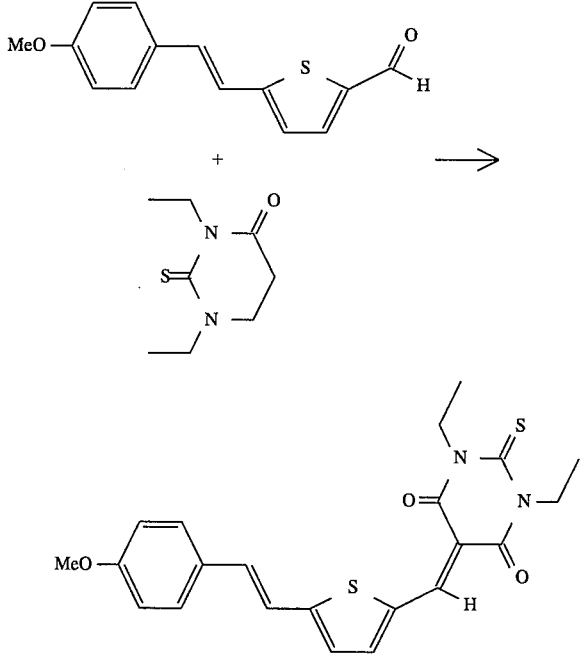

To 0.397 g (1.62 mmoles) of the product of Example 9 was added 5 ml of EtOH and 0.32 g (1.60 mmoles) of 1,3-diethyl-2-thiobarbituric acid and 5 drops of piperidine. The mixture was stirred overnight at room temperature. The red solid was filtered and washed with EtOH to give 0.597 g (1.40 mmoles, 87%) of the desired product. $^1H$ nmr($CD_2Cl_2$): 8.59 (s, 1H), 7.82 (d, J=4.2 Hz, 1H), 7.5 (m, 2H), 7.37 (d, J=16.1 Hz, 1H), 7.27 (d, J=4.2 Hz, 1H), 7.17 (d, J=16.1 Hz, 1H), 6.93 (m, 2H), 4.58 (m, 4H), 3.84 (s, 3H), 1.32 (m, 6H). Elemental analysis calculated for $C_{22}H_{22}N_2O_3S_2$: C: 61.95; H: 5.20. Found: C: 61.89; H: 5.28.

Example 11

Ten mg of the product of Example 10 and 50 mg of Polyimide C were dissolved in NMP and films were cast. The films were heated on a hot plate at 150° C. for 10 minutes and vacuum dried for 2 hours at 120° C. A film was poled at 159° C. and then cooled to 67° C. The field was removed and the sample placed in an 80° C. oven. The SHG signal at 80° C. was 40% of the maximum SHG signal observed during the poling process. This SHG signal decreased by about 1.1%/day at 80° C.

Example 12

Ten mg of the product of Example 10 and 50 mg of Polyimide B were dissolved in NMP and films were cast. The films were heated on a hot plate at 150° C. for 10 minutes and vacuum dried for 2 hours at 120° C. A film was poled at 187° C. and then cooled to 75° C. The field was removed and the sample placed in an 80° C. oven. The SHG signal at 80° C. was 41% of the maximum SHG signal observed during the poling process. This SHG signal decreased by about 1%/day at 80° C.

Example 13

1,3-Bisdicyanovinyl-2-(4-dimethylbenzyylidene)indane was prepared according to K. A. Bello, et al., J. Chem. Soc. Perkin Trans. II, 1987, p. 815. Fifteen mg of 1,3-bisdicyanovinyl-2-(4-dimethylbenzyylidene) indane and 50 mg of Polyimide C were dissolved in NMP and films were cast. The films were heated on a hot plate at 150° C. for 10 minutes and vacuum dried for ½ hours at 120° C. A film was poled at 160° C. and then cooled to 67° C. The field was removed and the sample placed in an 80° C. oven. The SHG signal at 80° C. was 69% of the maximum SHG signal observed during the poling process. This SHG signal decreased by about 0.6%/day at 80° C.

Particular embodiments of the invention are included in the examples. Other embodiments will become apparent to those skilled in the art from a consideration of the specification or practice of the invention disclosed herein. It is understood that the invention is not confined to the particular formulations and examples herein illustrated, but it embraces such modified forms thereof as come within the scope of the following claims.

What is claimed is:

1. A compound of the formula

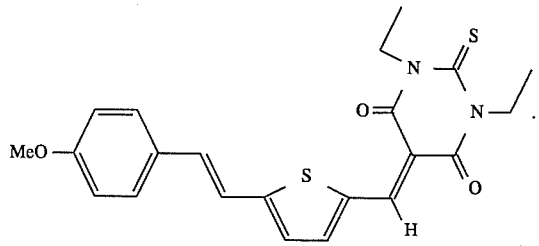

* * * * *